United States Patent [19]

LaNoue

[11] Patent Number: 5,300,298
[45] Date of Patent: Apr. 5, 1994

[54] METHODS OF TREATING OBESITY WITH PURINE RELATED COMPOUNDS

[75] Inventor: Kathryn F. LaNoue, Hershey, Pa.

[73] Assignee: The Pennsylvania Research Corporation, University Park, Pa.

[21] Appl. No.: 879,668

[22] Filed: May 6, 1992

[51] Int. Cl.$^5$ .......................... A23K 1/165; A23K 1/17
[52] U.S. Cl. ..................................... 424/442; 424/464; 514/261; 514/263; 514/866; 514/909
[58] Field of Search ................. 424/442; 514/909, 261, 514/263

[56] References Cited

U.S. PATENT DOCUMENTS

| | | | |
|---|---|---|---|
| 4,309,443 | 1/1982 | Smith | 514/909 |
| 4,761,421 | 8/1988 | Muir | 514/263 |
| 4,853,402 | 8/1989 | Bomann | 514/261 |
| 4,879,296 | 11/1989 | Daluge et al. | 514/263 |
| 4,981,857 | 1/1991 | Daluge et al. | 514/263 |
| 5,053,433 | 10/1991 | Philipposian | 514/909 |

OTHER PUBLICATIONS

S. J. Vannucci, et al., Am. J. Physiol., vol. 257 pp. E871-E878 (1989).
S. J. Vannucci, et al., Int'l. Journal of Obesity, vol. 14, pp. 125–134 (1990).
K. F. LaNoue, et al., In Role of adenosine and adenine nucleotides in the biological system, S. Imai & M. Nakazawa (ed.), Elsevier Science Publishers BV (1991).

Primary Examiner—Gabrielle Phelan
Attorney, Agent, or Firm—Thomas J. Monahan

[57] ABSTRACT

There is disclosed a method of treating obesity in warm-blooded animals, including humans, as well as a method of increasing the muscle mass to fat ratio in farm animals. The methods entail administering to an animal in need thereof, an effective amount of certain 8-phenylxanthines substituted in the 3- or 4-position of the phenyl group by an alkenylene, alkenyleneoxy, alkynylene or alkynyleneoxy bearing a terminal acetic grouping.

20 Claims, 7 Drawing Sheets

METHODS OF TREATING OBESITY WITH PURINE RELATED COMPOUNDS

FIELD OF THE INVENTION

The present invention pertains to a method of treating obesity in warm-blooded animals, including humans, and to methods of increasing the ratio of muscle mass to fat in farm animals.

BACKGROUND OF THE INVENTION

U.S. Pat. No. 4,879,296, issued Nov. 7, 1989 and U.S. Pat. No. 4,981,857, issued Jan. 1, 1991, disclose purine derivatives of Formula I described below, which are useful in the present invention. Methods of preparing the compounds are disclosed in both U.S. Pat. Nos. 4,879,296 and 4,981,857. The patents also disclose that the compounds provided therein are useful in human and veterinary therapy, particularly for conditions associated with the cell surface effects of adenosine. Even so, there is no disclosure in either U.S. patent that the compounds provided therein are useful as anti-obesity agents, or as agents capable of increasing the ratio to muscle mass to fat in farm animals. Instead, both patents are concerned with using the compounds disclosed therein in the treatment or prophylaxis of AIDS and other retroviral infections and for pathophysiological disorders arising from the cell surface effects of adenosine. Such pathophysiological disorders caused by adenosine/cell surface interaction are disclosed in both U.S. patents as including those arising within the cardiovascular, gastrointestinal or neuroendocrine systems, including heart block, asthma, and irritable bowel syndrome. U.S. Pat. No. 4,879,269 and 4,981,857 are each incorporated herein by reference, in their entirety.

SUMMARY OF THE INVENTION

The present invention provides a method of treating obesity in warm-blooded animals. In particular, the present invention provides a method of treating obesity (e.g., adult onset obesity, lifelong obesity and morbid obesity[7]) in humans. The method entails administering to a patient in need thereof, an effective amount of one of the anti-obesity agents encompassed by Formula I, as shown below. Such compounds are advantageously administered to a patient in need thereof in the form of a pharmaceutical composition, in combination with a pharmaceutically acceptable carrier.

Additionally, the compounds of Formula I can be used as an aide in treating a Type II diabetes condition in an obese patient. For example, many accepted treatments for Type II diabetic conditions often include weight reduction in an affected obese patient. Type II diabetes as used herein means non-insulin-dependent diabetes mellitus.

The present invention is also concerned with providing a method of increasing the ratio of muscle mass to fat in farm animals, by administering to such animals an effective amount of one of the compounds of Formula I, shown below. Exemplary of such farm animals are cattle, swine, sheep, fowl (including chickens and turkeys), horses and the like.

Compounds of Formula I, which are useful in the above described methods are as follows:

wherein:

$X_1$ and $X_2$ are the same or different and are hydrogen, $C_{1-6}$ alkyl, $C_{2-6}$ alkenyl or $C_{7-12}$ aralkyl optionally substituted in the aryl ring by $C_{1-6}$ alkyl, $C_{1-6}$ alkoxy, hydroxy, halo, nitro, amino, azido or cyano, provided that both $X_1$ and $X_2$ are not hydrogen;

one of $X_3$ and $X_4$ is hydrogen, $C_{1-6}$ alkyl, trifluoromethyl, $C_{1-6}$ alkoxy, halo, nitro, amino, $C_{1-6}$ alkoxycarbonyl or carboxy and the other is a group—Y—Z where Y is $C_{2-6}$ alkenylene, or $C_{3-6}$ alkenyleneoxy, $C_{2-6}$ alkynylene or $C_{3-6}$ alkynyleneoxy and Z is carboxy, sulphonyl or phosphonyl or a $C_{1-9}$ alkyl ester, a $C_{7-12}$ aralkyl ester or a $C_{6-12}$ aryl ester thereof, or a 5-tetrazolyl; and $X_5$ and $X_6$ are the same or different and are oxygen or sulphur; or a pharmaceutically acceptable salt thereof; or pharmaceutically acceptable solvate thereof.

The compounds of the invention may exist in a number of tautomeric forms and all such forms, individually and as mixtures, are embraced by the above definition of formula (I) even though only one tautomer is depicted for convenience.

Preferably, $X_1$ and $X_2$ are the same or different and are hydrogen or $C_{1-6}$ alkyl. In particular, $X_1$ and $X_2$ are the same or different and are both $C_{1-6}$ alkyl. Examples of $X_1$ and $X_2$, when $C_{1-6}$ alkyl, includes both branched and straight chain alkyl, for example methyl, ethyl, n- and isopropyl, and n-, iso- and tertbutyl. Preferred examples of $X_1$ and $X_2$ when $C_{1-6}$ alkyl, include ethyl, n-propyl and n-butyl, especially n-propyl.

Preferably, one of $X_3$ and $X_4$ is hydrogen.

A preferred subclass of Y is (in straight- or branched-chain form) $C_{2-3}$ alkenylene (such as vinylene, propenyleneoxy) or $C_{2-6}$ alkynylene (such as acetylene). Most preferably, Y is vinylene or acetylene.

Preferably, Z, when a $C_{1-9}$ alkyl ester, is a $C_{1-6}$ alkyl ester. Examples of Z, when a $C_{1-6}$ alkyl ester, include the methyl and ethyl esters.

Examples of Z, when a $C_{7-12}$ aralkyl ester, include the benzyl ester.

Examples of Z, when a $C_{6-12}$ aryl ester, include the phenyl ester.

As used herein in relation to the definition of Z, a phosphonyl ester includes both the dibasic ester and the monobasic half-ester.

As used herein, 5-tetrazoyl is the group having the structural formula:

which thus embraces both tautomeric forms thereof and which are identifiable as 5-(1H)-tetrazolyl and 5-(2H)-tetrazolyl.

Included within the definition of Z is a preferred subclass, wherein Z is carboxy, sulphonyl or phosphonyl or a $C_{1-6}$ alkyl ester thereof. Preferably, Z is carboxy or a $C_{1-6}$ alkyl, such as a methyl or ethyl, ester thereof.

Most preferably, $X_3$ is hydrogen and $X_4$ is the group —Y—Z where Y is vinylene and Z is carboxy.

Preferably, both $X_5$ and $X_6$ are oxygen.

The compounds of the present invention are capable of existing as geometric and optical isomers. All such isomers, individually and as mixtures, are included within the scope of the present invention. Compounds, in the form of the E-geometrical isomers, are particularly preferred.

Of the compounds exemplified hereinafter, those that are preferred include 1. (E)-4-(1,2,3,6-tetrahydro-2,6-dioxo-1,3-dipropyl-9H-purin-8-yl)cinnamic acid,
2. (E)-4-(1,2,3,6-tetrahydro-1,3-dimethyl-2,6-dioxo-9H-purin-8-yl)cinnamic acid,
3. (E)-4-(1,2,3,6-tetrahydro-3-methyl-2,6-dioxo-1-propyl-9H-purin-8-yl)cinnamic acid,
4. (E)-4-(1,3-diethyl-1,2,3,6-tetrahydro-2,6-dioxo-9H-purin-8-yl)cinnamic acid,
5. (E)-4-(1,3-diallyl-1,2,3,6-tetrahydro-2,6-dioxo-9H-purin-8-yl)cinnamic acid,
6. (E)-4-(1,2,3,6-tetrahydro-3-methyl-2,6-dioxo-9H-purin-8-yl)cinnamic acid,
7. (E)-4-(3-ethyl-1,2,3,6-tetrahydro-2,6-dioxo-9H-purin-8-yl)cinnamic acid,
8. (E)-4-(1,2,3,6-tetrahydro-2,6-dioxo-3-propyl-9H-purin-8-yl)cinnamic acid,
9. (E)-4-(1,2,3,6-tetrahydro-3-isobutyl-2,6-dioxo-9H-purin-8-yl)cinnamic acid,
10. (E)-4-(1,2,3,6-tetrahydro-1-methyl-2,6-dioxo-3-propyl-9H-purin-8-yl)cinnamic acid,
11. (E)-4-(1,2,3,6-tetrahydro-3-isobutyl-1-methyl-2,6-dioxo-9H-purin-8-yl)cinnamic acid,
12. (E)-4-(1-ethyl-1,2,3,6-tetrahydro-3-methyl-2,6-dioxo-9H-purin-8-yl)cinnamic acid,
13. (E)-4-(1,3-dibutyl-1,2,3,6-tetrahydro-1,6-dioxo-9H-purin-8-yl)cinnamic acid,
14. (E)-4-(1,3-dibenzyl-1,2,3,6-tetrahydro-2,6-dioxo-9H-purin-8-yl)cinnamic acid,
15. (E)-4-(3-butyl-1,2,3,6-tetrahydro-1-methyl-2,6-dioxo-9H-purin-8-yl)cinnamic acid.
16. (E)-4-(1-butyl-1,2,3,6-tetrahydro-3-methyl-2,6-dioxo-9H-purin-8-yl)cinnamic acid,
17. (E)-4-(3-benzyl-1,2,3,6-tetrahydro-1-methyl-2,6-dioxo-9H-purin-8-yl)cinnamic acid,
18. (E)-4-(1,2,3,6-tetrahydro-1,3-diisobutyl-2,6-dioxo-9H-purin-8-yl)cinnamic acid,
19. (E)-4-(1,2,3,6-tetrahydro-1,3-dimethyl-6-oxo-2-thio-9H-purin-8-yl)cinnamic acid,
20. (E)-4-[3-(4-cyanobenzyl)-1,2,3,6-tetrahydro-1-methyl-2,6-dioxo-9H-purin-8-yl]cinnamic acid,
21. (E)-4-[3-(3-cyanobenzyl)-1,2,3,6-tetrahydro-1-methyl-2,6-dioxo-9H-purin-8-yl]cinnamic acid,
22. 3-[4-(1,2,3,6-tetrahydro-2,6-dioxo-1,3-dipropyl-purin-8-yl) phenyl]propiolic acid,
23. (E)-4-[1-(4-cyanobenzyl)-1,2,3,6-tetrahydro-3-methyl-2,6-dioxo-9H-purin-8-yl]cinnamic acid,
24. (E)-4-(1-benzyl-1,2,3,6-tetrahydro-2,6-dioxo-3-propyl-9H-purin-8-yl)cinnamic acid,
25. (E)-4-(3-benzyl-1,2,3,6-tetrahydro-2,6-dioxo-1-propyl-9H-purin-8-yl)cinnamic acid.

Compound No. 1 is particularly preferred.

As salts of a compound of formula (I), there are included acid addition salts of the compound, wherein one of $X_3$ and $X_4$ is amino, and salts comprising the compound, wherein one of $X_3$ and $X_4$ is carboxy, or wherein the other is a group—Y—Z where Y is as hereinbefore defined and Z is carboxy, sulphonyl or phosphonyl, as an anionic species, together with a cation. In both types of salts, the pharmacological activity resides in the moiety derived from the compound of the invention as defined herein and the identity of the other component is of less importance although for therapeutic and/or commercial purposes it is, preferably, pharmaceutically acceptable to the recipient of the salt. Examples of pharmaceutically acceptable acid addition salts include those derived from mineral acids, such as hydrochloric, hydrobromic, phosphoric, metaphosphoric, nitric and sulphuric acids, and organic acids, such as tartaric, acetic, citric, malic, lactic, fumaric, benzoic, glycollic, gluconic, succinic and arylsulphonic, for example p-toluenesulphonic, acids. Examples of salts comprising the compound, wherein one of $X_3$ and $X_4$ is carboxy, or wherein the other is a group—Y—Z where Y is as hereinbefore defined and Z is carboxy, sulphonyl or phosphonyl, as an anionic species, together with a cation, include ammonium salts, alkali metal salts, such as sodium and potassium salts, alkaline earth salts, such as magnesium and calcium salts, and salts formed with organic bases, for example, amino salts derived from mono-, di- or tri-(lower alkyl) or (lower alkanol)amines, such as triethanolamine and diethylaminoethylamine, and salts with heterocyclic amines such as piperidine, pyridine, piperazine and morpholine.

Examples of a solvate of a compound of formula (I) or a salt thereof include hydrate, for example the monohydrate.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIG. 3: Glucose tolerance test after seven days of BW1433 administration. Animals were fasted overnight before injection of 1.25 g/Kg glucose and samples taken 15, 30, 60 and 120 min for glucose determinations. The conditions are the same as those described in legend to FIG. 2 (Cont=V). Panel 3A shows results for lean Zucker rats, Panel 3B shows results for obese Zucker rats.

FIG. 5: Body weights of lean and obese Zucker rats during chronic administration of BW1433. The data are presented as a % of day 0 weight. Day 0 represents when the Alzet mini-pumps were implanted. The conditions are the same as those described in the legend to FIG. 2. Panel 5A shows results for lean Zucker rats, Panel 5B shows results for obese Zucker rats.

DETAILED DESCRIPTION OF THE INVENTION

The following detailed description of the invention is provided as an aid to those desiring to practice the present invention. Even so, the following disclosure is not to be construed as limiting to the present invention, since minor variations and changes may be made in the preferred embodiments herein taught, without departing from the spirit or scope of the present inventive discovery. Based upon such considerations, the present invention is only to be limited by the scope of the claims appended hereto, and to the equivalents thereof.

Methods for preparing each of the Formula I compounds disclosed above, which compounds are useful in the present invention, are described in detail in U.S. Pat. Nos. 4,879,296 and 4,981,857. Thus, those desiring to practice the present invention should consult these two U.S. patents, should they desire to prepare compounds encompassed hereby. Additionally, it is noted that Burroughs Wellcome Co., Research Triangle Park, N.C., made available to the present inventors, one of the compounds useful herein. Namely, (E)-4-(1,2,3,6-tetrahydro-2,6-dioxo-1,3-dipropyl-9H-purin-8-yl)cinnamic acid. Internally, at Burroughs Wellcome, the compound is referred to as BW1433.

While it is possible for the compounds of the present invention and the salts and solvates thereof to be administered as the raw chemical, it is preferred to present them in the form of a pharmaceutical formulation and with appropriate carriers as the use may require Accordingly, in the present inventive methods pharmaceutical formulations may be utilized for human or veterinary application, which comprise a compound of the present invention, or a pharmaceutically acceptable salt or solvate thereof, and a pharmaceutically acceptable carrier therefor. Such pharmaceutical formulations may optionally contain other therapeutic agents that may usefully be employed in conjunction with the compound of the present invention, or a pharmaceutically acceptable salt or solvate thereof. The expression "pharmaceutically acceptable" as used herein in relation to the carrier is used in the sense of being compatible with the compound of the present invention, or a pharmaceutically acceptable salt or solvate thereof, employed in the formulation and with any other therapeutic agent that may be present, and not being detrimental to the recipient thereof. The carrier itself may constitute one or more excipients conventionally used in the art of pharmacy that enable a compound of the present invention, or a pharmaceutically acceptable salt or solvate thereof, and any other therapeutic agent that may be present, to be formulated as a pharmaceutical formulation.

The pharmaceutical formulations of the present invention include those suitable for oral, parenteral (including subcutaneous, intradermal, intramuscular and intravenous) and rectal administration although the most suitable route will probably depend upon, for example, the precise nature and severity of diabetes or obesity encountered and the identity of the recipient. The formulations may conveniently be presented in unit dosage form and may be prepared by any of the methods well known in the art of pharmacy All methods include the step of bringing into association the active ingredient, i.e. a compound of the present invention, or a pharmaceutically acceptable salt or solvate thereof, with a carrier. In general the formulations are prepared by uniformly and intimately bringing into association the active ingredient with a liquid carrier or, a finely divided solid carrier or both, and then, if necessary, forming the associated mixture into the desired formulation.

Pharmaceutical formulations of the present invention suitable for oral administration may be presented as discrete units, such as a capsule, cachet tablet, or lozenge, each containing a predetermined amount of the active ingredient; as a powder or granules; as a solution or a suspension in an aqueous liquid or a non-aqueous liquid such as syrup, elixir or a draught; or as an oil-in-water liquid emulsion or a water-in-oil liquid emulsion. The formulation may also be a bolus, electuary or paste.

Generally, a tablet is the most convenient pharmaceutical formulation suitable for oral administration. A tablet may be made by compressing or molding. Tablets may be prepared by compressing in a suitable machine the active ingredient in a free-flowing form, such as a powder or granules, in admixture with, for example, a binding agent, an inert diluent, a lubricating agent, a disintegrating agent and/or a surface active agent. Molded tablets may be prepared by molding in a suitable machine a mixture of the powdered active ingredient moistened with an inert liquid diluent. The tablets may optionally be coated or scored and may be formulated so as to provide slow or controlled release of the active ingredient.

The pharmaceutical formulations of the present invention suitable for parenteral administration include aqueous and non-aqueous sterile injection solutions which may contain, for example, an anti-oxidant, a buffer, a bacteriostat and a solute which renders the composition isotonic with the blood of the recipient, and aqueous and non-aqueous sterile suspensions which may contain, for example, a suspending agent and a thickening agent. The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

The pharmaceutical formulations of the present invention suitable for rectal administration may be presented as a suppository containing, for example, cocoa butter and polyethylene glycol.

An advantage of the compounds of the present invention and the pharmaceutically acceptable salts and solvates thereof is that they are generally water soluble and that, therefore, they are suitable for formulation as aqueous solutions. In contrast, a number of the various substituted 8-phenylxanthines of the prior art (*Biochem. Pharmac.* 1981, 30, 325 to 353; and *Proc. Nat. Acad. Sci.*, 1983, 80, 2077 to 2080) are not soluble in water or at least not sufficiently soluble so as to permit their formulation in this way.

The following Examples are provided as additional evidence of the utility of Applicant's Formula I compounds and the methods of the present invention. Nonetheless, the following example should not be construed to limit the present invention, since each of the above-described Formula I compounds are fully operative in the present inventive methods, even though certain compounds such as, 1,3-dipropyl-8-(p-acrylate) phenylxanthine (BW1433) are thought preferred in the present inventive methods. Moreover, the following Examples should not be deemed to unduly limit the present inventive discovery, based upon the test screening method utilized. In this respect, the screening method is indicative of a model of human morbid obesity and thus, positive results obtained in such a screening method portent to a utility in humans. The test method utilized hereinbelow is also effective in evidencing the utility of the test compounds in a method of increasing muscle mass to fat in farm animals, even though test subjects (rats) are not "farm animals," since the positive test results obtained in the screening method also portent to a utility in farm animals. Based upon such considerations, the following Examples are provided as an aide to those desiring to practice the present invention.

EXAMPLE I

Based upon some previous studies which demonstrated that A1 adenosine receptors are more active in adipocytes (fat cells) from obese Zucker rats than from lean rats[1-3], postulated that abnormally active A1 adenosine receptors might explain many of the metabolic abnormalities of obese Zucker rats. These abnormalities include excess adiposity, insulin resistance, poor glucose tolerance, sluggish lipolysis as well as poor thermogenic capacity. Based upon my postulation, I decided to study the effect of acute and chronic administration to obese Zucker rats of an A1-adenosine receptor antagonist encompassed by Formula I. In this respect, the metabolic abnormalities of the Zucker rat bear a striking similarity to those of morbidly obese humans and for this reason this obese rat strain has frequently been used as a model of human morbid obesity. It is well known that the obesity of this rat is the result of a single recessive gene mutation[4].

I chose to first test a Burroughs Wellcome compound BW1433[5] encompassed by Formula i, viz., (E)-4-(1,2,3,6-tetrahydro-2,6 dioxo-1, 3-dipropyl-9H-purin-8-yl)cinnamic acid as an A1-adenosine receptor antagonist because it does not penetrate the blood brain barrier and it can be administered and absorbed orally. My initial studies were carried out following acute subcutaneous injections of the drug into male Sprague Dawley rats and into lean and into obese Zucker rats. Blood samples (100 microliter) were taken from the tail of the rats and measurements made of serum glycerol[6]. Glycerol is an end product of lipolysis and thus an excellent indicator of the rate of whole body lipolysis. Since A1 adenosine receptors block lipolysis, activity of these receptors would be revealed by an increase in serum glycerol on administration of the blocker (antagonist). I discovered that in the absence of the Formula I compound tested, serum glycerol levels only differ slightly when comparing lean and obese animals. Since there is 3-4 times more fat in the obese animal this is good evidence for sluggish lipolysis per g of fat in the obese. The obese animals however seem to mobilize the fat at an earlier time after removal of their food supply (Table 1), since after 6 hours of fasting the obese serum glycerol levels are much higher than the lean.

Figure 1:
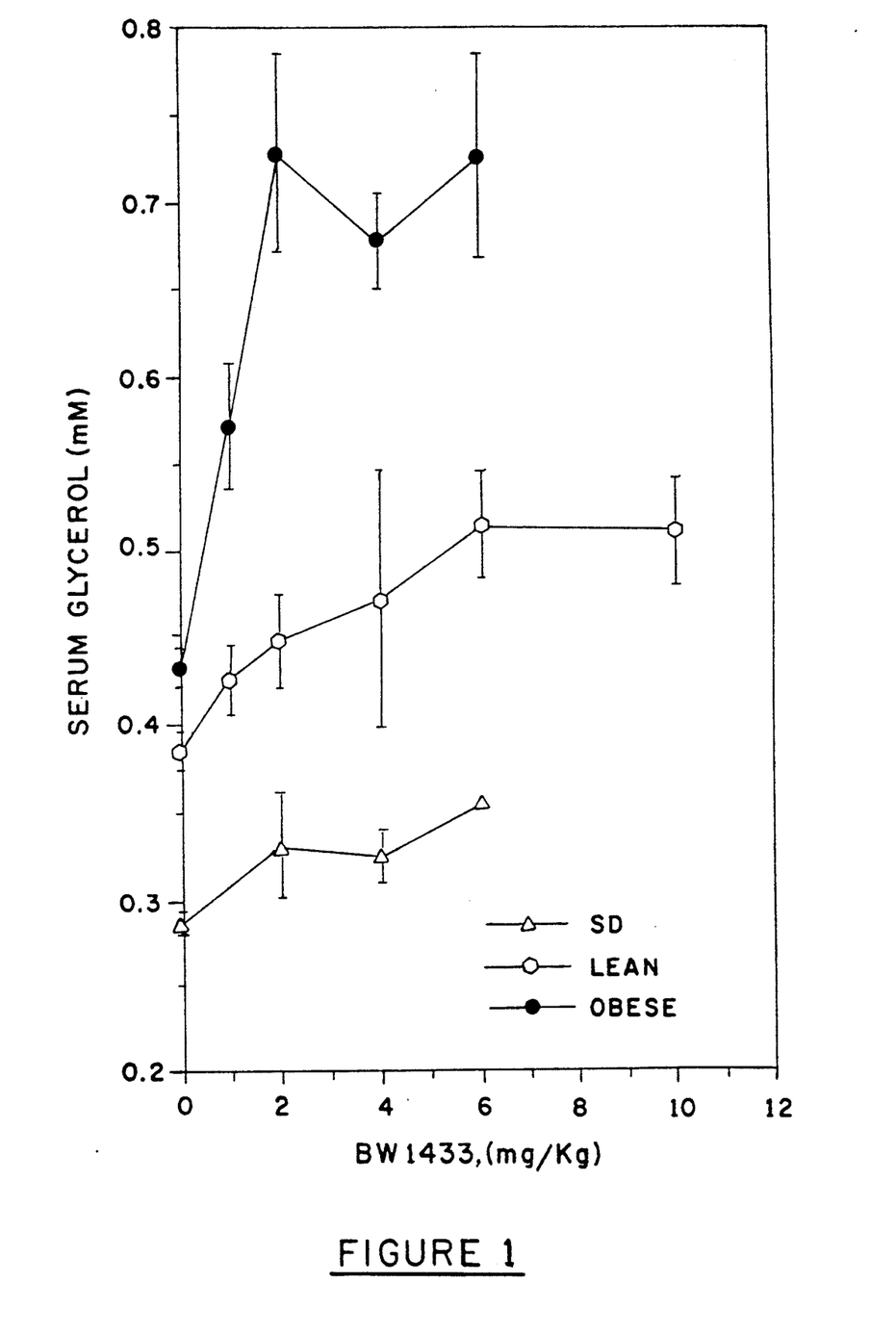
FIG. 1: Serum glycerol levels 60 min after a subcutaneous injection of BW1433 (0–10 mg/Kg) in Sprague Dawley rats (SD) and lean and obese Zucker rats. Each point represents 3–4 animals in the case of SD rats and 3–10 or 4–10 in the case of lean and obese Zuckers, respectively.

Next, I studied the effect of subcutaneous injections of BW1433 in 18 hour fasted animals. The results, shown in FIG. 1, support my initial postulation, that the A1 adenosine receptor may be particularly active in obese animals. Since the antagonist had little or no effect in the Sprague Dawley rats, it was either not an effective antagonist in these animals, or the receptor itself was inactive. To distinguish between these possibilities, the agonist N-6 phenylisopropyladenosine (PIA) was injected subcutaneously either alone or in combination with BW1433. Results obtained made it apparent that all three strains of rat have functional receptors in their fat cell membranes, and that these receptors could be effectively blocked with 1-2 mg/Kg of BW1433.

Next, I studied the effect of chronic treatment with BW1433. For this purpose I employed 2 ml Alzet mini osmotic pumps. Each pump was loaded with 2 ml of a solution containing BW1433 or with vehicle (aqueous solution adjusted to pH II). The amount of BW1433 was adjusted so that the pump delivered either zero, 0.2 mg or 0.4 mg/Kg/hour to each animal. On the first day the animals had the pumps implanted and were given a priming (2 mg/Kg or 4 mg/Kg) dose of the antagonist. Blood was taken prior to surgery and six hours after the animals were removed from their food supply. On each subsequent day animals had free access to food and water overnight, then their food removed for six hours, and a blood sample taken.

Figure 2:
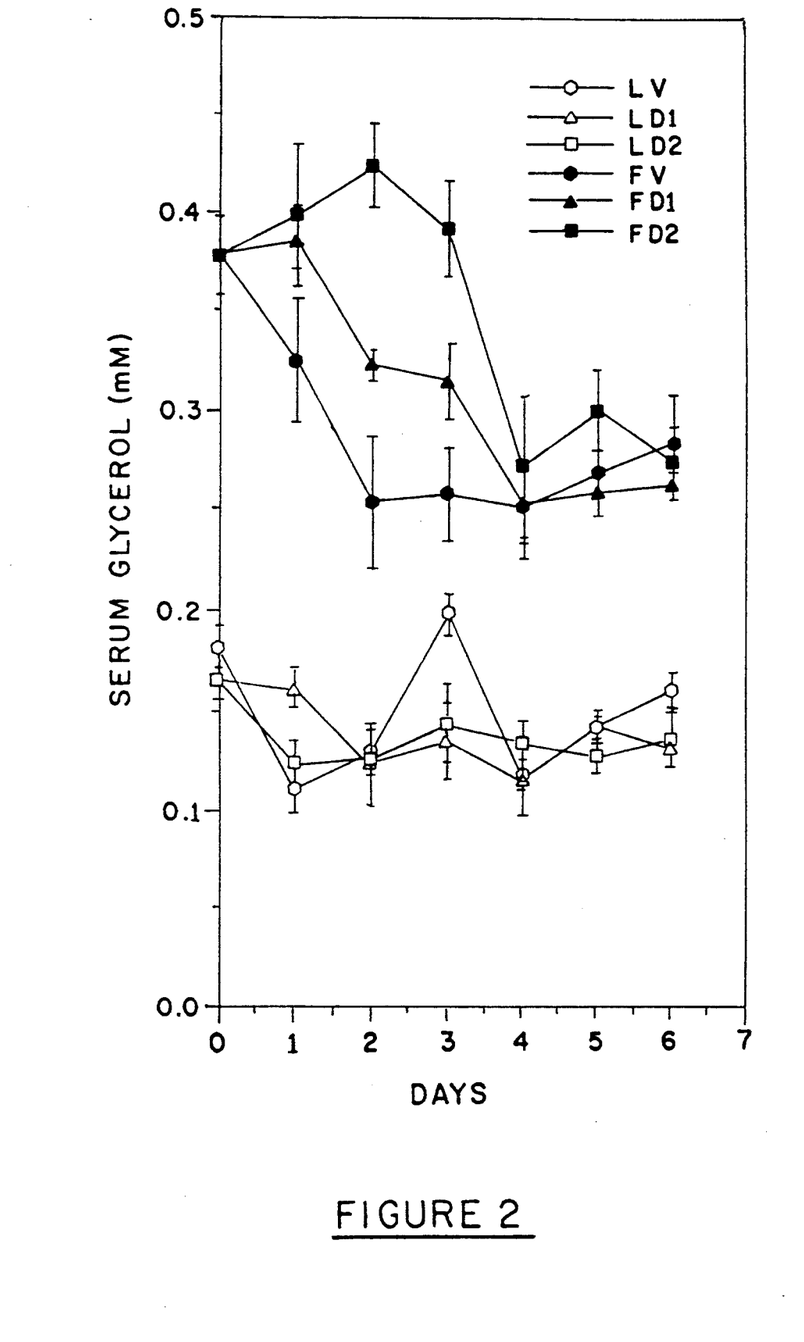
FIG. 2: Daily serum glycerol levels during chronic administration of BW1433 in lean (L) and obese (F) Zucker rats. In the no drug group (V) n=5, in the D1 group (0.2 mg/Kg/hr) n=5, and in the D2 group (0.4 mg/Kg/hr) n=4.
Figure 3A:
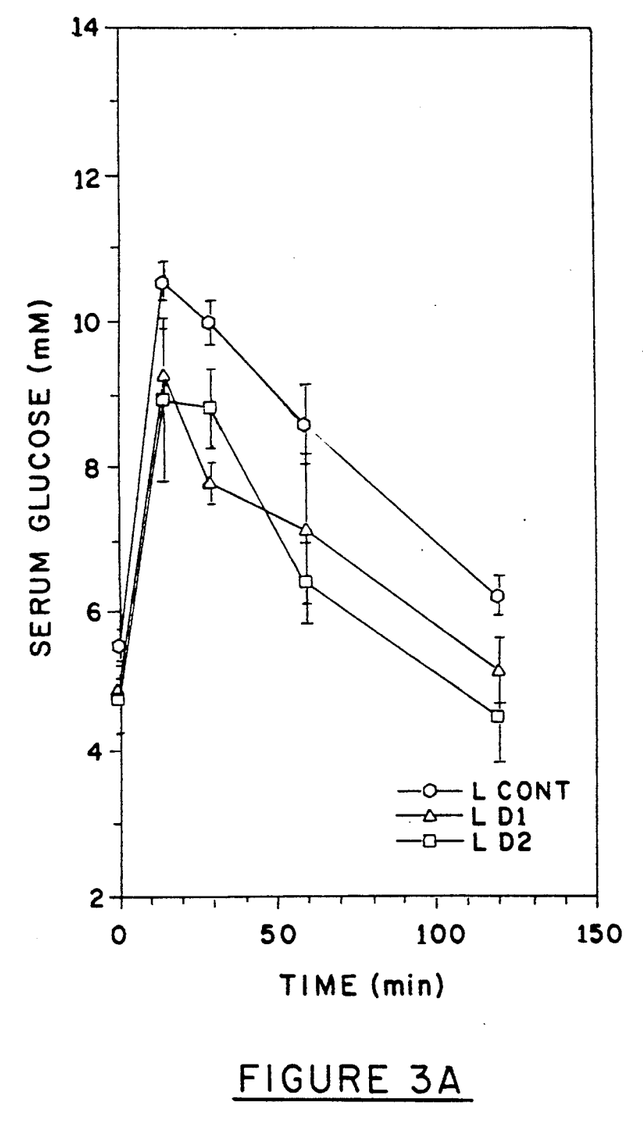
Figure 3B:
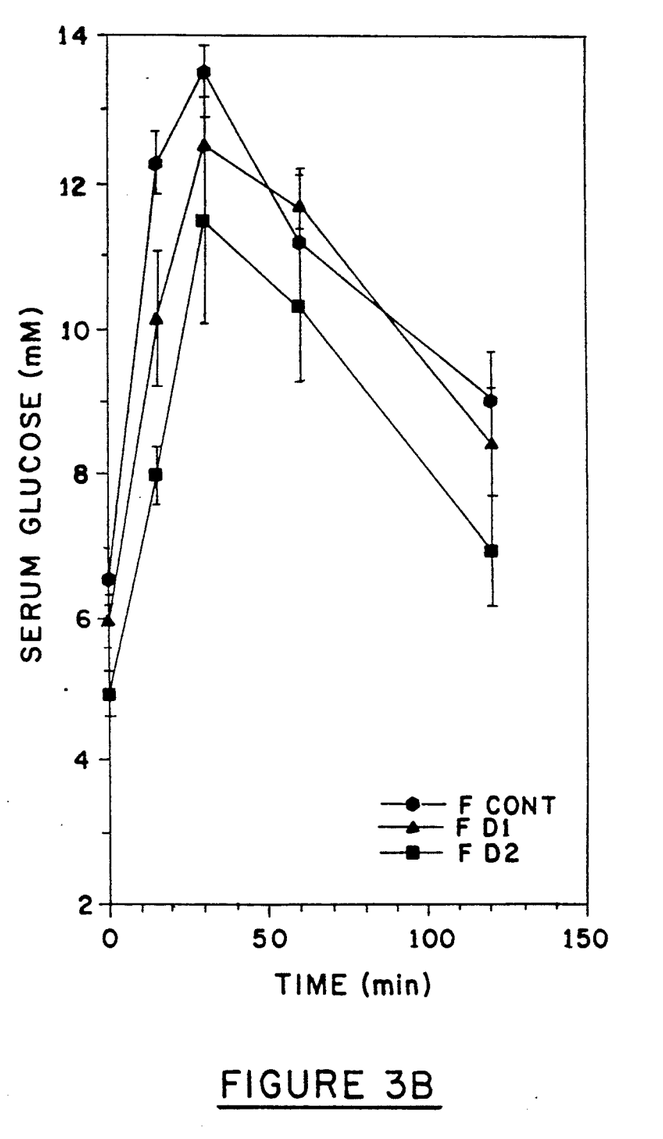
Figure 4:
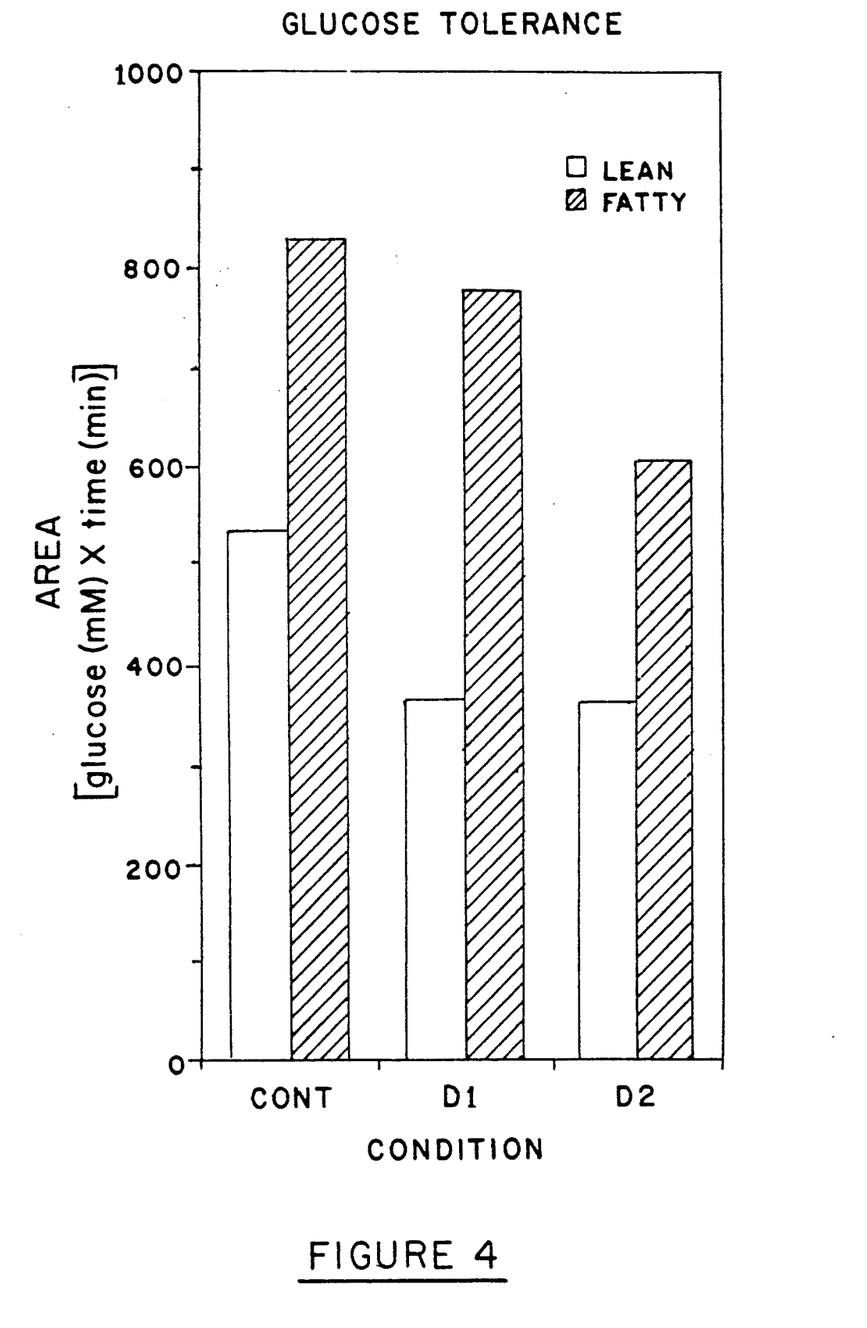
FIG. 4: A bar graph representing the area under the glucose tolerance curves of FIG. 3. The antagonist BW1433 does reduce the area under these curves in both lean and obese (fatty) animals.
Figure 5A:
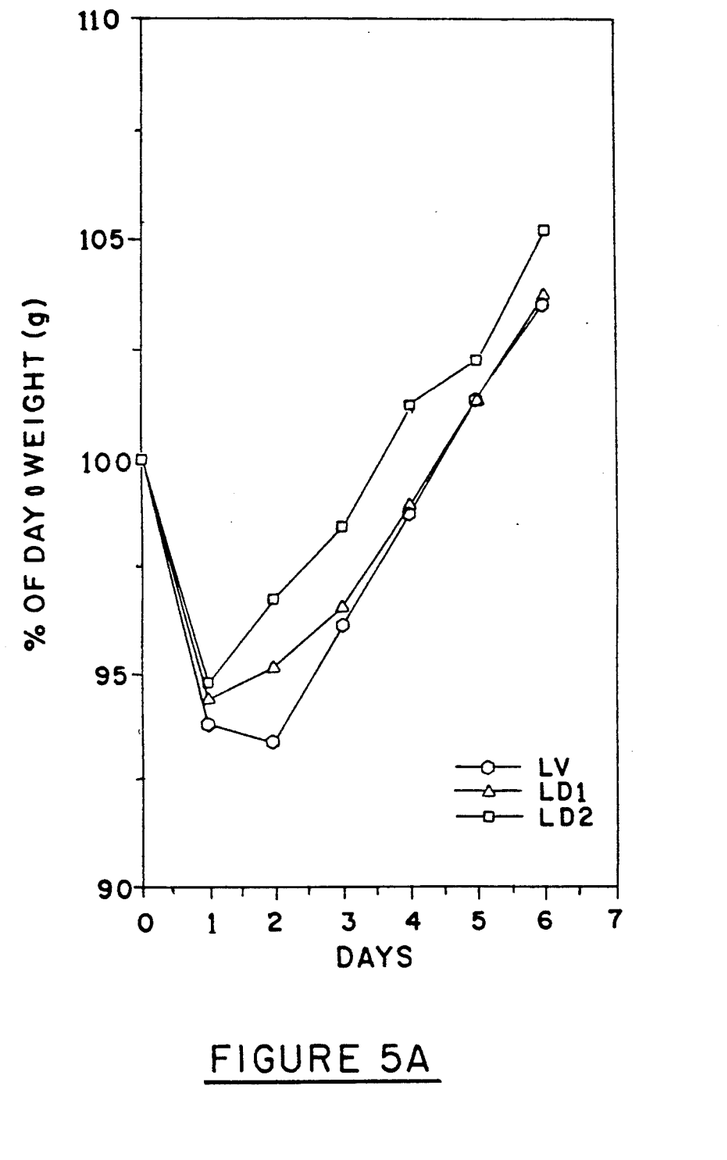
Figure 5B:
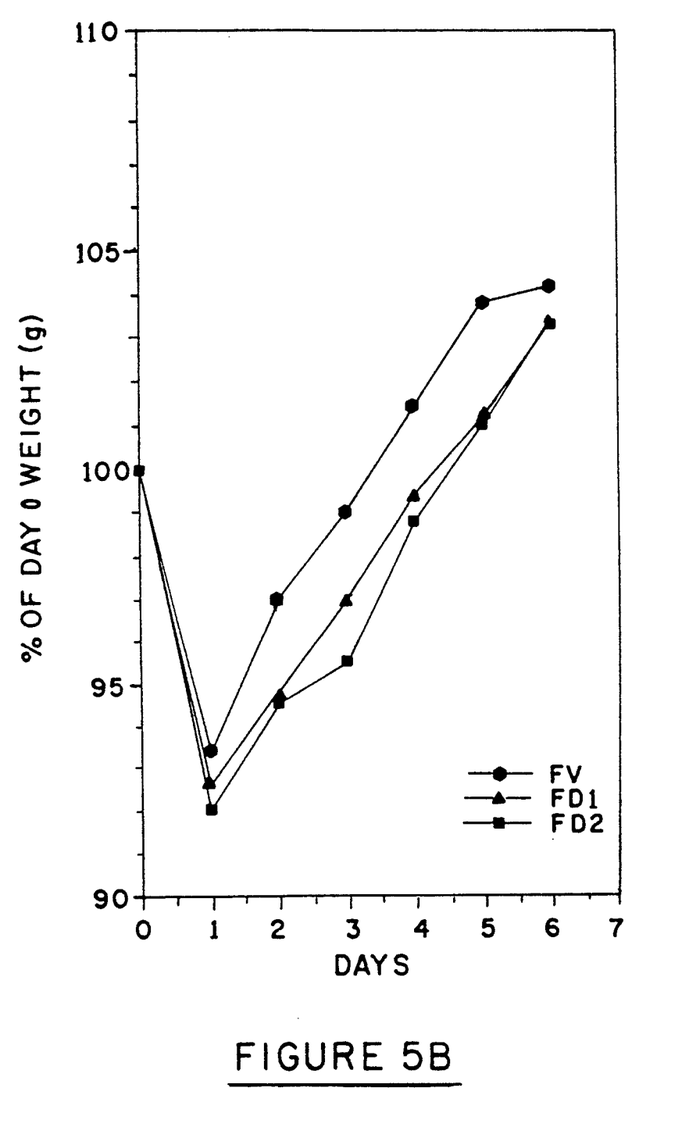

In addition to taking blood samples for glycerol analysis, each animal was weighed every day for seven days. After seven days the animals were fasted overnight and a glucose tolerance test given The animals were then sacrificed and 1 ml blood sample taken for serum insulin and serum BW1433 determination drug levels. Insulin levels were measured with RIA kit (Diagnostic Products) and BW1433 levels were measured fluorometrically after HPLC separation at Burroughs Wellcome, Research Triangle Park, North Carolina. FIG. 2 shows the results of the daily serum glycerol analysis. The drug did not effect the glycerol level of the lean animals. The serum glycerol levels of the control (no drug) obese animals decreased after two days on this study, possibly due to lowered anxiety and lowered serum catecholamines after "training." The drug treated obese animals had much higher levels of glycerol than the controls and serum levels were higher in the group with the higher dose of drug (0.4 mg/Kg) than those with the lower dose (0.2 mg/Kg). Some adaptation to the drug took place since all serum levels were similar on day 7. Nonetheless, when glucose tolerance curves were administered on day 7, drug-related differences could still be seen in all animals studied. FIG. 3 shows the serum glucose levels of the treated and of control animals following intraperitoneal administration of 1.25 g glucose/Kg. The area under the curve is smaller, the larger the dose of BW1433. This is illustrated more clearly in FIG. 4 where the area under the glucose tolerance curve is shown as a bar for each of the 6 groups of animals. Clearly the drug improved glucose tolerance. FIG. 5 is a chart of the change in weight of treated and untreated lean and obese animals. It is remarkable that the drug had opposite effects in the lean, and obese animals since it increased growth or weight gain in the lean, whereas it decreased growth or weight gain in the obese. The effect on weight change in each case was maximal at day 3, the day when the glycerol values peaked. Based on these remarkable results, the compounds of Formula I can be administered to obese warm-blooded animals as anti-obesity agents, or administered to farm animals to advantageously increase the ratio of muscle mass to fat therein.

Table II shows serum insulin levels in the six groups of animals. Table II also shows serum drug levels. The obese animals had somewhat higher levels of drug than the lean, though the two doses overlapped in lean and obese. The obese animals apparently have lower extracellular fluid volume per Kg body weight.

TABLE I

| STRAIN | FED(n) | FASTED (6 hrs.)(n) SERUM GLYCEROL (mM) | FASTED (18-20 hrs.)(n) |
|---|---|---|---|
| SPRAGUE DAWLEY | 0.104 ± 0.010(12) | — | 0.286 ± 0.007(79) |
| ZUCKER, LEAN | 0.117 ± 0.013(4) | 0.166 ± 0.011(15) | 0.385 ± 0.011(55) |
| ZUCKER, OBESE | 0.190 ± 0.011(4) | 0.378 ± 0.020(16) | 0.432 ± 0.011(51) |

TABLE II

| Condition | BW1433 micro g/ml | Insulin micro Iu/ml |
|---|---|---|
| Lean (Vehicle) | — | 7.92 ± 0.92 |
| Lean (+BW1433, 0.2 mg/kg) | 0.102 ± 0.020 | 11.63 ± 1.62 |
| Lean (+BW1433, 0.4 mg/kg) | 0.366 ± 0.098 | 10.67 ± 1.50 |
| Fatty (Vehicle) | — | 54.06 ± 9.49 |
| Fatty (+BW1433, 0.2 mg/kg) | 0.205 ± 0.022 | 52.81 ± 4.82 |
| Fatty (+BW1433, 0.4 mg/kg) | 0.624 ± 0.080 | 58.06 ± 6.52 |

EXAMPLE II

When each of the following Formula I compounds is tested as 1,3-propyl-8-(p-acrylate) phenylxanthine was tested in Example I, results are obtained which indicate that the compounds are active and effective in method of treating obesity in a warm-blooded animal and in a method of increasing the ratio of muscle mass to fat in farm animals:

(E)-4-(1,2,3,6-tetrahydro-1,3-dimethyl-2,6-dioxo-9H-purin-8-yl)cinnamic acid,
(E)-4-(1,2,3,6-tetrahydro-3-methyl-2,6-dioxo-1-propyl-9H-purin-8-yl)cinnamic acid,
(E)-4-(1,3-diethyl-1,2,3,6-tetrahydro-2,6-dioxo-9H-purin-8-yl)cinnamic acid,
(E)-4-(1,3-diallyl-1,2,3,6-tetrahydro-2,6-dioxo-9H-purin-8-yl)cinnamic acid,
(E)-4-(1,2,3,6-tetrahydro-3-methyl-2,6-dioxo-9H-purin-8-yl)cinnamic acid,
(E)-4-(3-ethyl-1,2,3,6-tetrahydro-2,6-dioxo-9H-purin-8-yl)cinnamic acid,
(E)-4-(1,2,3,6-tetrahydro-2,6-dioxo-3-propyl-9H-purin-8-yl)cinnamic acid,
(E)-4-(1,2,3,6-tetrahydro-3-isobutyl-2,6-dioxo-9H-purin-8-yl)cinnamic acid,
(E)-4-(1,2,3,6-tetrahydro-1-methyl-2,6-dioxo-3-propyl-9H-purin-8-yl)cinnamic acid,
(E)-4-(1,2,3,6-tetrahydro-3-isobutyl-1-methyl-2,6-dioxo-9H-purin-8yl)cinnamic acid,
(E)-4-(1-ethyl-1,2,3,6-tetrahydro-3-methyl-2,6-dioxo-9H-purin-8-yl)cinnamic acid,
(E)-4-(1,3-dibutyl-1,2,3,6-tetrahydro-2,6-dioxo-9H-purin-8-yl)cinnamic acid,
(E)-4-(1,3-dibenzyl-1,2,3,6-tetrahydro-2,6-dioxo-9H-purin-8-yl)cinnamic acid,
(E)-4-(3-butyl-1,2,3,6-tetrahydro-1-methyl-2,6-dioxo-9H-purin-8-yl)cinnamic acid.
(E)-4-(1-butyl-1,2,3,6-tetrahydro-3-methyl-2,6-dioxo-9H-purin-8-yl)cinnamic acid,
(E)-4-(3-benzyl-1,2,3,6-tetrahydro-1-methyl-2,6-dioxo-9H-purin-8-yl)cinnamic acid,
(E)-4-(1,2,3,6-tetrahydro-1,3-diisobutyl-2,6-dioxo-9H-purin-8-yl)cinnamic acid,
(E)-4-(1,2,3,6-tetrahydro-1,3-dimethyl-6-oxo-2-thio-9H-purin-8-yl)cinnamic acid,
(E)-4-[3-(4-cyanobenzyl)-1,2,3,6-tetrahydro-1-methyl-2,6-dioxo-9H-purin-8-yl]cinnamic acid,
(E)-4-[3-(3-cyanobenzyl)-1,2,3,6-tetrahydro-1-methyl-2,6-dioxo-9H-purin-8-yl]cinnamic acid,
3-[4-(1,2,3,6-tetrahydro-2,6-dioxo-1,3-dipropyl-9H-purin-8-yl)phenyl]propiolic acid,
(E)-4-[1-(4-cyanobenzyl)1,2,3,6-tetrahydro-3-methyl-2,6-dioxo-9H-purin-8-yl]cinnamic acid,
(E)-4-(1-benzyl-1,2,3,6-tetrahydro-2,6-dioxo-3-propyl-9H-purin-8-yl)cinnamic acid, and
(E)-4-(3-benzyl-1,2,3,6-tetrahydro-2,6-dioxo-1-propyl-9H-purin-8-yl)cinnamic acid.

Methods of preparation for each of the above compounds may be found in U.S. Pat. Nos. 4,879,296 and 4,981,857.

Pharmacology

The animal requiring treatment with a compound of the present invention, or a pharmaceutically acceptable salt or solvate thereof, is usually a human or non-human mammal.

The route by which the compound of the present invention, or a pharmaceutically acceptable salt or solvate thereof, is administered to the animal may be oral, parenteral (including subcutaneous, intradermal, intramuscular, intravenous) or rectal. If the compound of the present invention, or a pharmaceutically acceptable salt or solvate thereof, is presented in the form of a pharmaceutical formulation, which, as mentioned hereinbefore, is preferred, then the actual formulation employed will of course depend on the route of administration elected by the physician or veterinarian. For example, if oral administration is preferred, then the pharmaceutical formulation employed is, preferably, one which is suitable for such a route.

A therapeutically effective amount of a compound of the present invention, or a pharmaceutically acceptable salt or solvate thereof, will depend upon a number of factors including, for example, the age and weight of the animal, the obese condition or diabetic condition requiring treatment and its severity, and the route of administration, and will ultimately be at the discretion of the attendant physician or veterinarian. However, an effective amount of a compound of the present invention for the treatment of obesity or to increase the ratio of muscle mass to fat in a farm animal, will generally be in the range of 0.1 to 50 mg/Kg body weight of recipient per day, more usually in the range of 0.5 to 10 mg/Kg body weight per day and most often in the range of 1 to 5 mg/Kg body weight per day. Thus, for a 70 Kg adult patient, the actual amount per day would most often be from 70 to 350 mg and this amount may be given in a single dose per day or more usually in a number (such as two, three or four) of sub-doses per day such that the total daily dose is the same.

An effective amount of a pharmaceutically acceptable salt or solvate of a compound of the present invention may be determined as a proportion of the effective amount of the compound per se.

When compounds of Formula I are administered to farm animals to increase the ratio of muscle mass to fat therein, it is envisioned that pharmaceutical compositions such as described above can be utilized. Oral administration of the compositions is preferred. If desired, the compounds of Formula I and/or pharmaceutical formulations can be incorporated into an animal's feed to facilitate administration of the compound. Use of a feed premix containing a compound of Formula I, is encompassed herein. Such premixes should allow the Formula I compounds to remain stable and active prior to consumption by an intended farm animal, should be physiologically acceptable for use with farm animals, and should allow those skilled in the art to easily administer an effective amount of a Formula I compound to a farm animal to increase the animal's muscle mass to fat ratio.

The invention thus being described, it will be obvious that the same may be varied in many ways. Such variations are not to be regarded as a departure from the spirit and scope of the invention, and all such modifications as would be obvious to one skilled in the art are intended to be included within the scope of the following claims. Each of the publications and patents referred to herein are expressly incorporated herein by reference in their entirety.

References

1. Vannucci, S. J., Klim, C. M., Martin, L. F., and LaNoue, K. F. A1-adenosine receptor-mediated inhibition of adipocyte adenylate cyclase and lipolysis in Zucker rats. *Am. J. Physiol.* 257:E871–E878, 1989.
2. Vannucci, S. J., Klim, C. M., LaNoue, K. F., and Martin, L. F. Regulation of fat cell adenylate cyclase in young Zucker rats. Alterations in GTP sensitivity of $A_1$ adenosine mediated inhibition. *Int. J. Obesity* 14:125–134, 1991.
3. LaNoue, K. F., Vannucci, S. J., Robishaw-Neely, J., and Martin, L. F. Adenosine receptor malfunction in fa/fa Zucker rats. A role in obesity. In: Role of adenosine and adenine nucleotides in the biological system. (Imai, S. and Nakazawa, M. eds.) Elsevier Science Publishers, pp. 487–498.
4. Greenwood, M. R. C., and Turkenkoff, I. J. In: *Contemporary Issues in Clinical Nutrition*, Vol. IV: Obesity. (M. R. C. Greenwood, ed.) Churchill Livingston, N.Y. pp. 193–208.
5. Linden, J. Structure and function of 1 adenosine receptors. *FASEB J.* 5:2668–2676, 1991.
6. Eggstein, M., and Kuhlman. Triglycerides and Glycerol. In: *Methods of Enzymatic Analysis* (Bermeyer, H. U., ed.) New York, Academic Press, pp. 1825–1831.
7. Dorland's Pocket Medical Dictionary, 24th Ed., p. 429, W. B. Saunders Co., Harcourt Brace Jovanovich, Inc. Philadelphia, Pa. (1989).

What is claimed is:

1. A method of treating obesity in a warm-blooded animal, the method comprising administering to said animal:
   an effective anti-obesity amount of a compound of Formula I wherein:

$X_1$ and $X_2$ are the same or different and are hydrogen, $C_{1-6}$ alkyl, $C_{2-6}$ alkenyl or $C_{7-12}$ aralkyl optionally substituted in the aryl ring by $C_{1-6}$ alkyl, $C_{1-6}$ alkoxy, hydroxy, halo, nitro, amino, azido or cyano, provided that both $X_1$ and $X_2$ are not hydrogen;

one of $X_3$ and $X_4$ is hydrogen, $C_{1-6}$ alkyl, trifluoromethyl, $C_{1-6}$ alkoxy, halo, nitro, amino, $C_{1-6}$ alkoxycarbonyl or carboxy and the other is a group—Y—Z where Y is $C_{2-6}$ alkenylene, or $C_{3-6}$ alkenyleneoxy, $C_{2-6}$ alkynylene or $C_{3-6}$ alkynyleneoxy and Z is carboxy, sulphonyl or phosphonyl or a $C_{1-9}$ alkyl ester, a $C_{7-12}$ aralkyl ester or a $C_{6-12}$ aryl ester thereof, or a 5-tetrazolyl; and $X_5$ and $X_6$ are the same or different and are oxygen or sulphur; or a pharmaceutically acceptable salt thereof; or pharmaceutically acceptable solvate thereof.

2. The method of claim 1 wherein said Formula I compound which is administered in an effective anti-obesity amount is:

(E)-4-(1,2,3,6-tetrahydro-2,6-dioxo-1,3-dipropyl-9H-purin-8-yl)cinnamic acid, (E)-4-(1,2,3,6-tetrahydro-1,3-dimethyl-2,6-dioxo-9H-purin-8-yl)cinnamic acid, (E)-4-(1,2,3,6-tetrahydro-3-methyl-2,6-dioxo-1-propyl-9H-purin-8-yl)cinnamic acid, (E)-4-(1,3-diethyl-1,2,3,6-tetrahydro-2,6-dioxo-9H-purin-8-yl)cinnamic acid, (E)-4-(1,3-diallyl-1,2,3,6tetrahydro-2,6-dioxo-9H-purin-8-yl)cinnamic acid, (E)-4-(1,2,3,6-tetrahydro-3-methyl-2,6-dioxo-9H-purin-8-yl)cinnamic acid, (E)-4-(3-ethyl-1,2,3,6-tetrahydro-2,6-dioxo-9H-purin-8-yl)cinnamic acid, (E)-4-(1,2,3,6-tetrahydro-2,6-dioxo-3-propyl-9H-purin-8-yl)cinnamic acid, (E)-4-(1,2,3,6-tetrahydro-3-isobutyl-2,6-dioxo-9H-purin-8-yl)cinnamic acid, (E)-4-(1,2,3,6-tetrahydro-1-methyl-2,6-dioxo-3-propyl-9H-purin-8-yl)cinnamic acid, (E)-4-(1,2,3,6-tetrahydro-3-isobutyl-1-methyl-2,6-dioxo-9H-purin-8-yl)cinnamic acid, (E)-4-(1-ethyl-1,2,3,6-tetrahydro-3-methyl-2,6-dioxo-9H-purin-8-yl)cinnamic acid, (E)-4-(1,3-dibutyl-1,2,3,6-tetrahydro-2,6-dioxo-9H-purin-8-yl)cinnamic acid, (E)-4-(1,3-dibenzyl-1,2,3,6-tetrahydro-2,6-dioxo--purin-8-yl)cinnamic acid, (E)-4-(3-butyl-1,2,3,6-tetrahydro-1-methyl-2,6-dioxo-9H-purin-8-yl)cinnamic acid.

(E)-4-(1-butyl-1,2,3,6-tetrahydro-3-methyl-2,6-dioxo-9H-purin-8-yl)cinnamic acid, (E)-4-(3-benzyl-1,2,3,6-tetrahydro-1-methyl-2,6-dioxo-9H-purin-8-yl)cinnamic acid, (E)-4-(1,2,3,6-tetrahydro-1,3-diisobutyl-2,6-dioxo--purin-8-yl)cinnamic acid, (E)-4-(1,2,3,6-tetrahydro-1,3-dimethyl-6-oxo-2-thio-9H-purin-8-yl)cinnamic acid,
(E)-4-]3-(4-cyanobenzyl)-1,2,3,6-tetrahydro-1-methyl-2,6-dioxo-9H-purin-8-yl]cinnamic acid,
(E)-4-[3-(3-cyanobenzyl)-1,2,3,6-tetrahydro-1-methyl-2,6-dioxo-9H-purin-8-yl]cinnamic acid,
3-[4-(1,2,3,6-tetrahydro-2,6-dioxo-1,3-dipropyl-9H-purin-8-yl)phenyl]propiolic acid,
(E)-4-[1-(4-cyanobenzyl)-1,2,3,6-tetrahydro-3-methyl-2,6-dioxo-9H-purin-8-yl]cinnamic acid,
(E)-4-(1-benzyl-1,2,3,6-tetrahydro-2,6-dioxo-3-propyl-9H-purin-8-yl)cinnamic acid, or
(E)-4-(3-benzyl-1,2,3,6-tetrahydro-2,6-dioxo-1-propyl-9H-purin-8-yl)cinnamic acid; or a salt or solvate thereof.

3. The method of claim 1, wherein said Formula I compound which is administered in an effective anti-obesity amount is:
(E)-4-(1,2,3,6-tetrahydro-2,6-dioxo-1,3-dipropyl-9H-purin-8-yl)cinnamic acid; or a salt or solvate thereof.

4. The method of claim 1, wherein said Formula I compound is administered in the form of a pharmaceutical composition further comprising a pharmaceutically acceptable carrier.

5. The method of claim 4, wherein said pharmaceutical composition is in a form suitable for oral administration.

6. The method of claim 5, wherein said pharmaceutical composition is in the form of a tablet.

7. The method of claim 1, wherein said Formula I compound is administered to said warm-blooded animal in an amount of 0.1 to 50 mg/Kg/day based on said animal's body weight.

8. The method f claim 1, wherein said Formula I compound is administered to said warm-blooded animal in an amount of 0.5 to 10 mg/Kg/day based on said animal's body weight.

9. The method of claim 1, wherein said warm-blooded animal is a human.

10. The method of claim 1, wherein said warm-blooded animal is an obese human afflicted with a Type II diabetic condition.

11. A method of increasing the ratio of muscle mass to fat in a farm animal, the method comprising administering to said animal:
an effective amount of a Formula I compound for increasing the ratio of muscle mass to fat in said animal wherein:
$X_1$ and $X_2$ are the same or different and are hydrogen, $C_{1-6}$ alkyl, $C_{2-6}$ alkenyl or $C_{7-12}$ aralkyl optionally substituted in the aryl ring by $C_{1-6}$ alkyl, $C_{1-6}$ alkoxy, hydroxy, halo, nitro, amino azido or cyano, provided that both $X_1$ and $X_2$ are not hydrogen;
one of $X_3$ and $X_4$ is hydrogen, $C_{1-6}$ alkyl, trifluoromethyl, $C_{1-6}$ alkoxy, halo, nitro, amino, $C_{1-6}$ alkoxycarbonyl or carboxy and the other is a group —X—Z where Y is $C_{2-6}$ alkenylene, or $C_{3-6}$ alkenyleneoxy, $C_{2-6}$ alkynylene or $C_{3-6}$ alkynyleneoxy and Z is carboxy, sulphonyl or phosphonyl or a $C_{1-9}$ alkyl ester, a $C_{7-12}$ aralkyl ester or a $C_{6-12}$ aryl ester thereof, or a 5-tetrazolyl; and
$X_5$ and $X_6$ are the same or different and are oxygen or sulphur; or a pharmaceutically acceptable salt thereof; or a pharmaceutically acceptable solvate thereof.

12. The method of claim 11, wherein said farm animal is a cow, a pig, a sheep, a horse, a chicken or a turkey.

13. The method of claim 11, wherein said Formula I compound which is administered is:
(E)-4-(1,2,3,6-tetrahydro-2,6-dioxo-1,3-dipropyl-9H-purin-8-yl)cinnamic acid,
(E)-4-(1,2,3,6-tetrahydro-1,3-dimethyl-2,6-dioxo-9H-purin-8-yl)cinnamic acid,
(E)-4-(1,2,3,6-tetrahydro-3-methyl-2,6-dioxo-1-propyl-9H-purin-8-yl)cinnamic acid,
(E)-4-(1,3-diethyl-1,2,3,6-tetrahydro-2,6-dioxo-9H-purin-8-yl)cinnamic acid,
(E)-4-(1,3-diallyl-1,2,3,6-tetrahydro-2,6-dioxo-9H-purin-8-yl)cinnamic acid,
(E)-4-(1,2,3,6-tetrahydro-3-methyl-2,6-dioxo-9H-purin-8-yl)cinnamic acid,
(E)-4-(3-ethyl-1,2,3,6-tetrahydro-2,6-dioxo-9H-purin-8-yl)cinnamic acid,
(E)-4-(1,2,3,6-tetrahydro-3-methyl-2,6-dioxo-9H-purin-8-yl)cinnamic acid,
(E)-4-(1,2,3,6-tetrahydro-3-isobutyl-2,6-dioxo-9H-purin-8-yl)cinnamic acid,
(E)-4-(1,2,3,6-tetrahydro-1-methyl-2,6-dioxo-3-propyl-9H-purin-8-yl)cinnamic acid,
(E)-4-(1,2,3,6-tetrahydro-3-isobutyl-1-methyl-2,6-dioxo-9H-purin-8-yl)cinnamic acid,
(E)-4-(1-ethyl-1,2,3,6-tetrahydro-3-methyl-2,6-dioxo-9H-purin-8-yl)cinnamic acid,
(E)-4-(1,3-dibutyl-1,2,3,6-tetrahydro-2,6-dioxo-9H-purin-8-yl)cinnamic acid,
(E)-4-(1,3-dibenzyl-1,2,3,6-tetrahydro-2,6-dioxo-9H-purin-8-yl)cinnamic acid,
(E)-4-(3-butyl-1,2,3,6-tetrahydro-1-methyl-2,6-dioxo-9H-purin-8-yl)cinnamic acid.
(E)-4-(1-butyl-1,2,3,6-tetrahydro-3-methyl-2,6-dioxo-9H-purin-8-yl) cinnamic acid,
(E)-4-(3-benzyl-1,2,3,6-tetrahydro-1-methyl-2,6-dioxo-9H-purin-8yl)cinnamic acid,
(E)-4-(1,2,3,6-tetrahydro-1,3diisobutyl-2,6-dioxo-9H-purin-8-yl)cinnamic acid,
(E)-4-(1,2,3,6-tetrahydro-1,3-dimethyl-6-oxo-2-thio-9H-purin-8-yl)cinnamic acid,
(E)-4-[3-(4-cyanobenzyl)-1,2,3,6-tetrahydro-1-methyl-2,6-dioxo-9H-purin-8-yl]cinnamic acid,
(E)-4-[3-(3-cyanobenzyl)-1,2,3,6-tetrahydro-1-methyl-2,6-dioxo-9H-purin-8-yl]cinnamic acid,
3-[4-(1,2,3,6-tetrahydro-2,6-dioxo-1,3-dipropyl-9H-purin-8-yl) phenyl]propiolic acid,
(E)-4-[1(4-cyanobenzyl)-1,2,3,6-tetrahydro-3-methyl-2,6-dioxo-9H-purin-8yl]cinnamic acid,
(E)-4-(1-benzyl-1,2,3,6-tetrahydro-2,6-dioxo-3-propyl-9H-purin-8yl) cinnamic acid, or
(E)-4-(3-benzyl-1,2,3,6-tetrahydro-2,6-dioxo-1-propyl-9H-purin-8-yl) cinnamic acid; or a slat or solvate thereof.

14. The method of claim 11, wherein said Formula I compound which is administered is:
(E)-4-(1,2,3,6-tetrahydro-2,6-dioxo-1,3-dipropyl-9H-purin-8yl)cinnamic acid; or a slat or solvate thereof.

15. The method of claim 11, wherein said Formula I compound is administered int he form of a pharmaceutical composition further comprising a pharmaceutically acceptable carrier.

16. The method of claim 15, wherein said pharmaceutical composition is in a form suitable for oral administration.

17. The method of claim 16, wherein said pharmaceutical composition is in the form of a tablet.

18. The method of claim 11, wherein said Formula I compound is administered to sad farm animal in an amount of 0.1 to 50 mg/Kg/day based on said animal's body weight.

19. The method of claim 11, wherein said Formula I compound is administered to said farm animal in an amount of 0.5 to 10 mg/Kg/day based on said animal's body weight.

20. The method of claim 11, wherein said Formula I compound is administered to said farm animal in the animal's feed.

* * * * *

UNITED STATES PATENT AND TRADEMARK OFFICE
CERTIFICATE OF CORRECTION

PATENT NO. : 5,300,298 Page 1 of 1
DATED : April 5, 1994
INVENTOR(S) : Kathryn F. LaNoue It is certified that error appears in the above-identified patent and that said Letters Patent is hereby corrected as shown below:

Column 1,
Line 5, after the title, and before "FIELD OF THE INVENTION" insert the following:

-- GOVERNMENT SPONSORSHIP

The present invention was supported by the National Institutes of Health and the American Heart Association under Grant No. R01 DK44070. Accordingly, the U.S. government may have certain rights in this invention. --

Signed and Sealed this

Eleventh Day of March, 2003

JAMES E. ROGAN
*Director of the United States Patent and Trademark Office*